United States Patent [19]
Wenman et al.

[11] Patent Number: 5,987,982
[45] Date of Patent: Nov. 23, 1999

[54] BALANCE PERFORMANCE MONITOR

[75] Inventors: Alan Wenman, Dunmow; Christopher Daughtery, Bishops Stortford, both of United Kingdom

[73] Assignee: SMS Sandland Manufacturing Services Limited, United Kingdom

[21] Appl. No.: 08/923,835

[22] Filed: Sep. 4, 1997

Related U.S. Application Data

[63] Continuation of application No. 08/325,314, filed as application No. PCT/GB93/00847, Apr. 22, 1993.

[51] Int. Cl.$^6$ .......................................................... A61B 5/22
[52] U.S. Cl. ........................... 73/379.08; 482/9; 434/253; 73/172
[58] Field of Search .............................. 73/462, 457, 172, 73/379.01, 379.05, 379.08, 379.09; 434/253; 482/1, 4, 8, 9

[56] References Cited

U.S. PATENT DOCUMENTS

| | | | |
|---|---|---|---|
| 4,151,839 | 5/1979 | Schwarz | 601/104 |
| 4,669,722 | 6/1987 | Rangaswamy | 482/79 |
| 4,760,850 | 8/1988 | Phillips et al. | 607/49 |
| 4,986,534 | 1/1991 | Meier et al. | 482/8 |
| 5,049,079 | 9/1991 | Furtado et al. | 482/4 |

*Primary Examiner*—Max Noori
*Attorney, Agent, or Firm*—Andrus, Sceales, Starke & Sawall

[57] ABSTRACT

An apparatus and a method to monitor the balance performance of a user comprises two separate but similar foot-plates each slightly larger than the foot of a user. Each foot-plate includes detectors to detect the load imparted to the foot-plate by a user, about two axes generally at right angles with one axis lying more or less along the length of the user's foot and the other axis transverse thereto. The outputs from the foot-plates are fed to a processing unit which drives a display device, graphically to show to the user on a real-time basis the detected loads and so to allow a user to modify his balance performance.

15 Claims, 5 Drawing Sheets

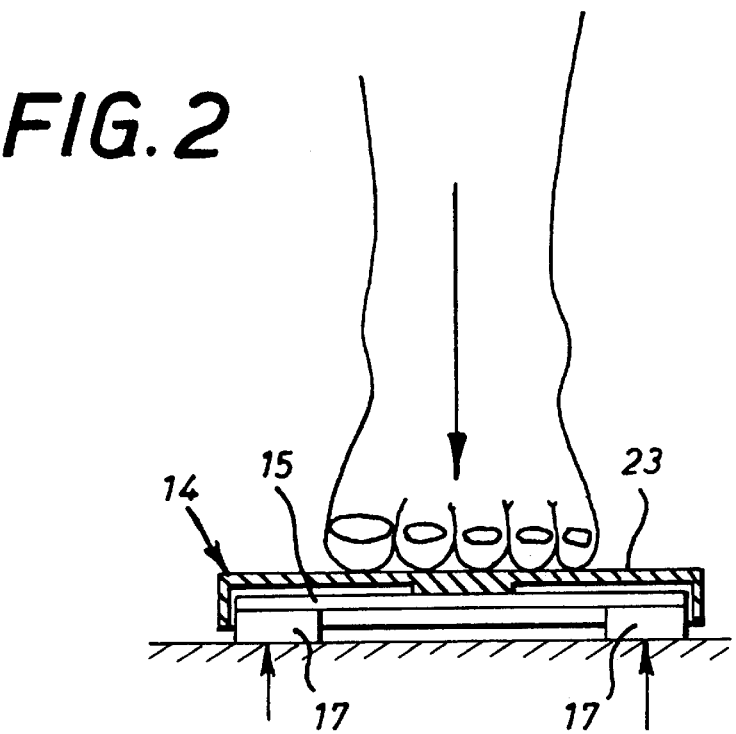
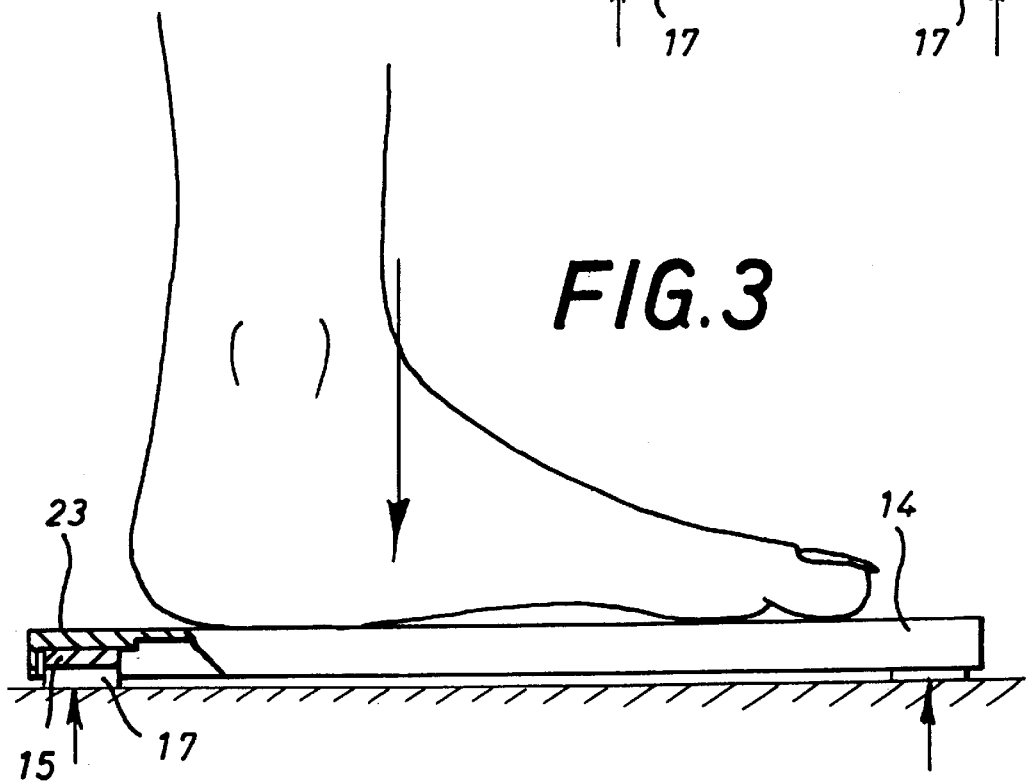

BALANCE PERFORMANCE MONITOR

This application is a continuation of application Ser. No. 08,325,314 filed Oct. 24, 1994, now abandoned which is a 371 of PCT/GB93/00847 filed on Apr. 22, 1993.

This invention relates to apparatus for monitoring the balance performance of a user, suitable for use for example in physiotherapy as well as in other medical circumstances, in sports both to assist recovery from an injury and to improve performance, and in other fields.

It has been established that the posture and gait of a person can often be improved by monitoring the load carried by each foot, and then displaying essentially in real time those loads to the person in such a way that he may himself adjust the loads until they become substantially the same. In effect, a closed-loop system is set up allowing a user to observe and correct primarily his balance and perhaps also his posture. It is found that if a person suffers for example from disease of the joints or from post-injury trauma, the loads carried by the two feet may differ greatly, but by allowing a person to monitor those loads himself the manner described above, rapid improvements in the condition from which the user is suffering may be obtained.

Following extended research into balance and posture, it has now been determined that further and more rapid improvements are possible if the user is supplied with even more information concerning the loading on his two feet, and specifically concerning the front-to-back loading and the side-to-side loading, for each foot. Thus, the present invention provides apparatus to monitor the balance performance of a user, which apparatus comprises a pair of foot-plates upon which the user may stand with one foot on each foot-plate respectively, each foot-plate including means to detect the load imparted thereto by the user about two axes generally at right angles, one axis lying generally along the length of a user's foot and the other transverse to the length thereof, the apparatus further comprising means to display graphically the detected loads.

The load-detecting means associated with each foot-plate could take a variety of forms, but for many users it may be particularly important that the foot-plate has the smallest possible vertical height above a supporting surface, to minimise the vertical lift a user has to impart to his foot in order to stand on the foot-plate. This may be achieved by having the load-detecting means of each foot-plate in the form of a plurality of load cells disposed beneath the foot-plate, each load cell providing an electrical output dependent upon the load applied thereto. Preferably, however, each foot-plate is supported by a pair of resilient beams provided with strain detectors (gauges) which permit an assessment of the loading on the foot-plate, both in the front-to-back and side-to-side directions. Thus, each foot-plate may be provided with load-detecting means which are disposed to detect the loading substantially at the four corners of a rectangle which encloses the area of the foot-plate upon which a user should stand. In effect, two load-detecting means may be provided at the front of the foot-plate, disposed one to each side thereof, and two load-detecting means at the back of the foot-plate again with one to each side of the foot-plate. Alternatively, the load-detecting means may be arranged at the points of a diamond, with two such means on the front-to-back axis and two on the side-to-side axis. In either case, the foot-plate may conveniently be marked to show the approximate position where a user's foot should be placed and the orientation thereof.

In order that a user may gain optimum benefit from apparatus of this invention, it is important that a user may readily associate his balance performance with the display thereof. To this end, the display means may include a pictorial representation of at least one foot, but preferably of both feet, each such representation including two series of indicators extending respectively along and transverse to the representation, and which indicators are successively activated dependent upon the output of the load-detecting means. Where there are representations of both feet, then there may be a further series of indictors arranged to represent a comparison of the load imparted by a user to each of the two foot-plates. In this way, a user may monitor the relative loading on his two feet, as well as the front-to-back and side-to-side loading of each foot.

As an alternative, the graphical display may be computer generated and be displayed on a visual display unit. In such a case, various techniques may be employed to show relative loadings, such as the use of colour or different intensities of colour; other techniques will readily suggest themselves to those skilled in the art.

The outputs from the load-detecting devices of the two foot-plates should be suitably processed to yield signals suitable for driving the display means. In a case where each load-detecting device comprises four load cells or strain detectors, it would be possible to combine the individual load cell or detector outputs by a hard-wired controller circuit, though it is convenient to employ a computer to combine the outputs in the appropriate ways. In this case, the analogue outputs from the load cells or detectors may be converted to digital signals for processing by the computer, the computer then driving the display means.

Where a computer is employed to process the data derived from the load-detecting means of each foot-plate, the computer may be used to yield other valuable data to assist an assessment of balance performance. For example, apart from driving a real-time display of balance for viewing by a user, an assessment of "balance performance" and "sway co-efficient" may be made and displayed. Data may be stored from a period of use of the apparatus by one user, and then further processed for instance to show average loadings. Also, responses to certain stimuli—such as if the user is pushed in some direction—may be monitored and analysed, as may the performance of a user on performing some task, such as swinging a golf club, a racket or the like. A computer may also be used to provide an interface to a printer, for giving a permanent record of balance performance data.

This invention also extends to a method of providing a user with a real-time indication of his balance performance, comprising: standing the user on a pair of foot-plates each configured to detect the loadings imparted thereto about two axes at right-angles to each other; detecting the front-to-back loading and side-to-side loading imparted by each foot of the user on the respective foot-plate; and processing the detected loadings to drive a graphical display device illustrating to the user his actual balance performance in relation to an ideal performance.

By way of example only, one specific embodiment of balance performance monitoring apparatus constructed and arranged in accordance with the present invention will now be described in detail, reference being made to the accompanying drawings, in which:

FIG. 2 is a vertical sectional view of a foot-plate used in apparatus of FIG. 1;

FIG. 3 is a side view of the foot-plate of FIG. 1;

Figure 1:
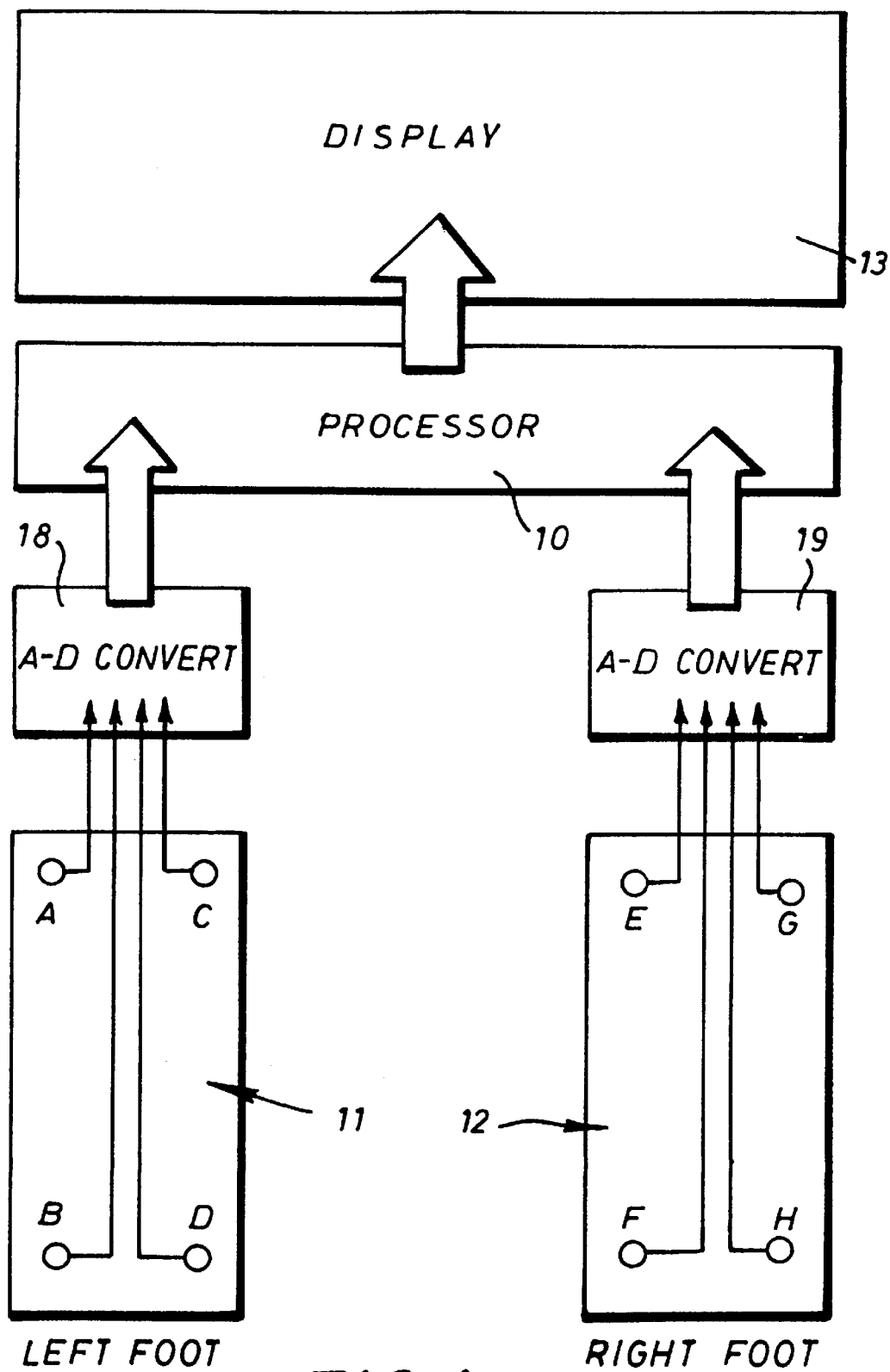
FIG. 1 is a block diagram of a complete balance performance monitoring apparatus of this invention.
Figure 5:
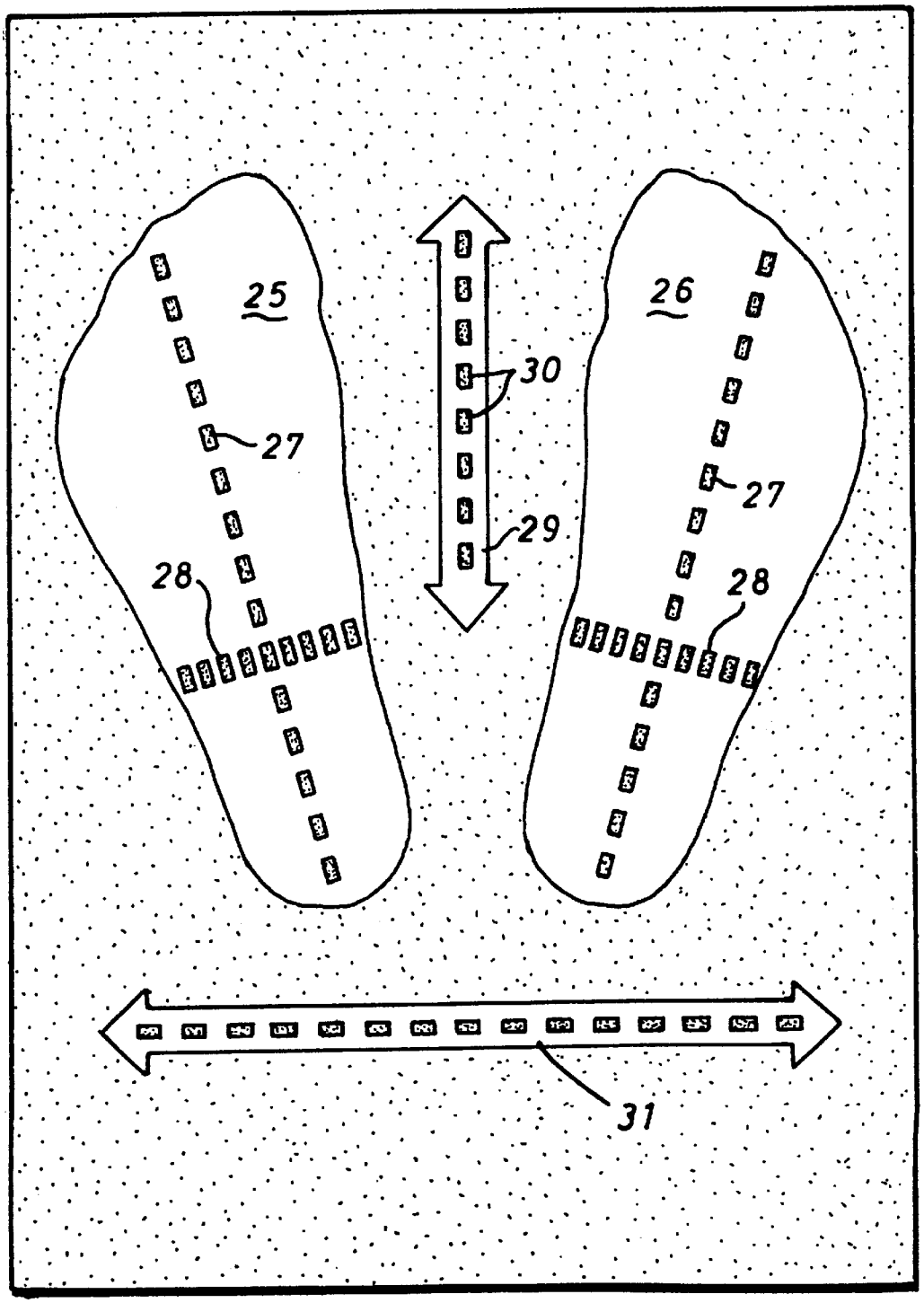
FIGS. 5 and 6 show two alternative display devices for use in the apparatus of FIG. 1.

Referring initially to FIG. 1, there is shown a block diagram of balance performance monitoring apparatus of this invention, which apparatus employs a computer 10 running an appropriate programme to process data derived from load-measuring points A, B, C and D, and E, F, G and H, of two foot-plates 11 and 12 respectively. The computer 10 is arranged to drive a display device 13, which may take the form of a specially configured display, such as is shown in FIG. 5, or may more generally take the form of a video display unit (VDU) driven by the computer so as graphically to show the processed data.

Figure 4:
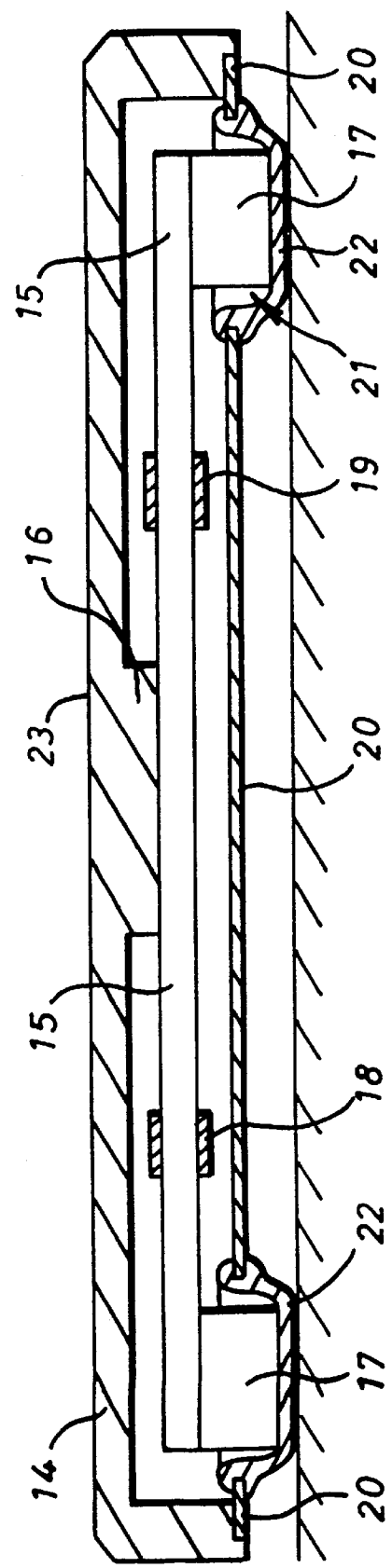
FIG. 4 is a vertical section through the foot-plate of FIGS. 2 and 3, on an enlarged scale.

Each foot-plate 11 and 12, shown in more detail in FIGS. 2, 3 and 4, comprises a rigid plate 14 of a rectangular shape, and of a size slightly greater than the largest human foot likely to be encountered. Arranged at each end of the foot-plate is a transverse resilient beam 15, rigidly attached to a downwardly-projection boss 16 formed in the underside of the foot-plate. The free ends of each beam are provided with legs 17, and pairs of strain gauges 18 and 19 are mounted on the beams, to each side of the boss 16. A coverplate 20 is attached to the underside of the plate 14, which cover plate has apertures 21 to receive the legs 17. Flexible sealing boots 22 are fitted in the apertures 21 to extend over the legs 17. It is preferred for the upper surface 23 of each plate 14 to carry a diagrammatic representation of a foot, arranged centrally on that plate 14, so that a user will naturally tend to place his foot symmetrically on the plate, as shown in FIGS. 2 and 3, rather than to one side or to one end of the plate.

The outputs obtained from each strain gauge of a pair are combined to give four outputs from points A to D of plate 11 and E to H of the plate 12, indicative of the loading at those points. These outputs are supplied to respective analogue digital converters 18 and 19, the digital outputs of which are then fed to the computer 10, for processing therewithin. The programme on which the computer runs is arranged to allow a display of the relative loads carried by the left and right feet, as well as the side-to-side weight distribution for each foot, independently, and the front to back weight distribution, again for each foot independently.

In order to allow a display of the balance between the two feet, the computer processes and displays the comparison of:

(A+B+C+D):(E+F+G+H)

In order to allow a display of the side-to-side weight distribution within the left foot, the computer processes and displays the comparison of:

(A+B):(C+D)

For the right foot, the computer processes and displays the comparison of:

(E+F):(G+H)

In a similar way, the computer allows the display of the front to rear weight distribution, independently for the left and right feet by processing and displaying the results of the comparisons:

(A+C):(B+D)—for the left foot;

and (E+G):(F+H)—for the right foot.

A typical screen display for illustrating the results of the above comparisons is shown in FIG. 5, comprising the front panel of an adjustable stand which panel is printed with diagrammatic representations of the left and right feet 25 and 26. Mounted behind the panel are, for each foot representation, light emitting diodes arranged in two lines 27 and 28, line 27 extending generally centrally along the length of the foot representation, and line 28 transversely thereto. The two lines of light emitting diodes intersect in the region of the approximate centre of pressure of a "normal" person. The display further includes a fore and aft arrow 29 arranged between the representations of the two feet, within which arrow extends a further line 30 of light emitting diodes. Yet another arrow 31 is arranged on the display apparatus to extend from left-to-right between representations of the two feet, there being a line of light emitting diodes within that line.

When the overall apparatus is in use in conjunction with the display device of FIG. 5, the appropriate light emitting diode may be illuminated by the computer 10, in order to show how the weight of a user is distributed over his two feet. Moreover, the light emitting diodes within the arrow 31 may appropriately be illuminated to show how the weight is distributed between the two feet of the user. Arrow 29 would not ordinarily be employed when the apparatus is being used just with two foot-plates; it may be used when a seat is connected to the computer 10, to show weight distribution on that seat, in conjunction with arrow 31. Such a seat (not shown) may have four sensors arranged somewhat similarly to those of each foot-plate, and the computer would assess left-to-right balance and front-to-rear balance of a person sitting on that seat, and then display the results of the assessments on the display device.

Figure 6:
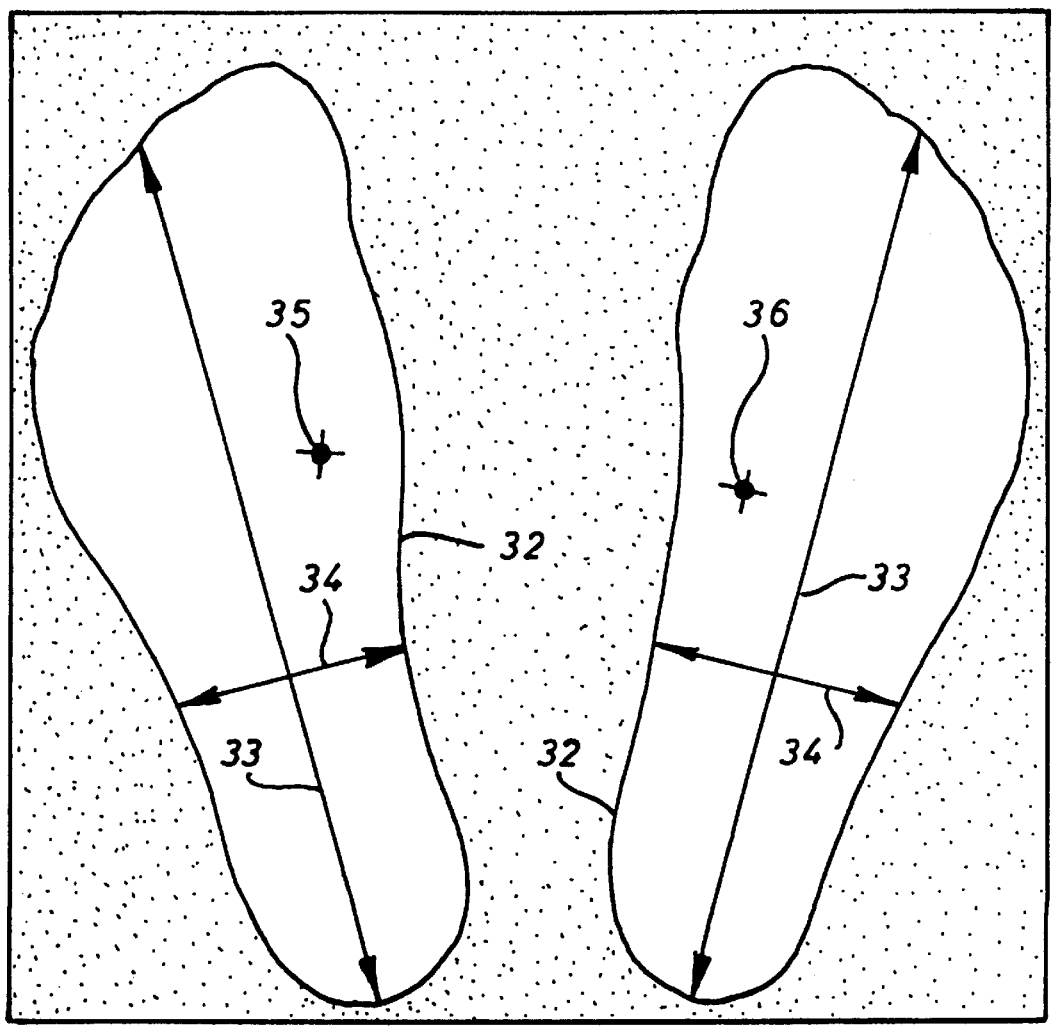

FIG. 6 shows an alternative display, such as may be generated by a computer driving a VDU screen. The computer would produce diagrammatic representations 32 of the two feet together with two datum axes 33 and 34, the points of intersection of which being at the centre of pressure referred to above, for a "normal" person. The computer may also generate markers 35 and 36 to show where the user actually has his centres of pressure, for each of his two feet.

By viewing either of the two screen displays described above, when using the apparatus, a person may adjust his posture and observe the effect of that adjustment; in this way, a person may seek to improve his posture so as to achieve a centre of pressure more closely matched to the ideal position. A trained operator (clinician) may also use the apparatus, for an assessment of the subtalar (ankle) joint position, and for knee assessment and an analysis of abnormal gait. The apparatus may further be used for re-training, for example following soft tissue injury to the ankle, which tends to be repetitive in many patients. For this, one foot-plate may be used, with the patient balancing on one foot, on that foot-plate, and leaning rapidly and effectively to correct any deviations from the correct balance.

We claim:

1. Apparatus to monitor the balance performance of a human user, which apparatus comprises:

a pair of independent foot-plates upon which the user may stand with one foot on one foot-plate and the other foot on the other foot-plate, each foot-plate having an indication of the general position over which a user's foot should be placed and having means to detect the load imparted to the foot-plate by the user, said load-detecting means associated with each foot-plate being arranged to detect the load imparted to the respective foot-plate about a first axis lying generally along the length of a user's foot from toes to heel correctly placed with respect to the foot position indication and simultaneously to detect the load imparted to the foot-plate about a second axis generally at right angles to the first axis; and display means to display the load imparted to each foot-plate, said display means includes a representation of the user's feet and displays in a graphical manner, for each foot-plate separately but simultaneously, the position of the detected loads with respect to the representation of a user's feet;

wherein the display means continuously and simultaneously displays both the position of the load between the user's toes and heel for each foot and the side-to-side position of the load along the second axis for each foot to determine the balance performance for the human user.

2. Apparatus according to claim 1, wherein each foot-plate is supported by a pair of spaced resilient beams provided with strain detectors which provide outputs depending upon the loading on the foot-plate.

3. Apparatus according to claim 1, wherein the load-detecting means of each foot-plate comprises a plurality of load cells disposed beneath the foot-plate, each load cell providing an electrical output dependent upon the load applied thereto.

4. Apparatus according to claim 2, wherein each foot-plate is provided with load-detecting means arranged to detect loading substantially at the four corners of a rectangle which encloses the area of the foot-plate upon which a user should stand.

5. Apparatus according to claim 2, wherein each foot-plate is provided with load-detecting means arranged to detect loading at the points of a diamond, with two points on the front-to-back axis and two on the side-to-side axis of the foot-plate.

6. Apparatus according to claim 1, wherein each foot-plate is marked to show the approximate position where a user's foot should be placed and the orientation thereof.

7. Apparatus according to claim 1, wherein the display means includes a pictorial representation of at least one foot together with two series of indicators extending respectively along and transverse to the representation, and which indicators are successively activated dependent upon the output of the load-detecting means.

8. Apparatus according to claim 7, wherein there are pictorial representations of two feet, each having two series of indicators extending respectively along and transverse to the respective representation.

9. Apparatus according to claim 7, wherein there is a further series of indictors arranged to represent a comparison of the load imparted by a user to each of the two foot-plates.

10. Apparatus according to claim 1, wherein the graphical display is computer-generated and is displayed on a visual display unit.

11. Apparatus according to claim 1, wherein there is additionally provided a seat having load-detecting means arranged to permit an assessment of the left-to-right balance and the front-to-rear balance of a person sitting on that seat, the outputs from the seat additionally being supplied to said display means for display thereon.

12. Apparatus according to claim 1, wherein the outputs from the load-detecting means of the two foot-plates are supplied to computer apparatus programmed to combine the outputs from the load-detecting means in the appropriate ways.

13. A method of providing a human user with a real-time indication of the user's balance performance, comprising:

standing the user on a pair of independent foot-plates with one foot on one foot-plate and the other foot on the other foot-plate, each foot-plate having an indication of the general position over which a user's foot should be placed and each being configured to detect the load imparted to the foot-plate by the user about a first and second axes substantially at right angles with the first axis lying generally along the length of a user's foot from toes to heel correctly placed with respect to the foot position indication;

separately detecting the load imparted to each foot-plate about said first axis thereof and simultaneously about said second axis generally at right angles to the first axis; and providing a graphical display device which includes a representation of the user's feet and continuously displaying on said graphical display device, for each foot-plate separately but simultaneously, the load imparted on each foot-plate and the position of the detected loads along both the first axis and the second axis for each foot such that the position of the load between the user's toes and heel for each foot and the side-to-side position of the load along the second axis for each foot are displayed to determine the balance performance of the human user.

14. Apparatus according to claim 3, wherein each foot-plate is provided with load-detecting means arranged to detect loading substantially at the four corners of a rectangle which encloses the area of the foot-plate upon which a user should stand.

15. Apparatus according to claim 3, wherein each foot-plate is provided with load detecting means arranged to detect loading at the points of a diamond, with two points on the front-to-back axis and two on the side-to-side axis of the foot-plate.

\* \* \* \* \*